(12) United States Patent  (10) Patent No.: US 7,392,903 B2
Jolley et al.  (45) Date of Patent: Jul. 1, 2008

(54) BEDSIDE DISPOSAL OF CONTAMINATED SHARPS

(75) Inventors: Scott Jolley, Ogden, UT (US); Chris Jolley, Scottsdale, AZ (US)

(73) Assignee: Safe Solutions, Inc., Scottsdale, AZ (US)

( * ) Notice: Subject to any disclaimer, the term of this patent is extended or adjusted under 35 U.S.C. 154(b) by 460 days.

(21) Appl. No.: 10/992,630

(22) Filed: Nov. 18, 2004

(65) Prior Publication Data

US 2005/0103663 A1    May 19, 2005

Related U.S. Application Data

(60) Provisional application No. 60/523,251, filed on Nov. 18, 2003.

(51) Int. Cl.
*B65D 83/10* (2006.01)

(52) U.S. Cl. .................. 206/366; 206/363; 206/438; 206/822

(58) Field of Classification Search ......... 206/363–370, 206/223, 570, 571, 438, 822, 1.5; 220/DIG. 13, 220/259.1, 259.2, 256.1, 375, 229, 826, 833, 220/834, 836, 837, 839, 324
See application file for complete search history.

(56) References Cited

U.S. PATENT DOCUMENTS

| | | | | |
|---|---|---|---|---|
| 1,559,624 A | * | 11/1925 | Kopp | 220/610 |
| 4,061,226 A | * | 12/1977 | Essen | 206/306 |
| 4,494,652 A | * | 1/1985 | Nelson et al. | 206/366 |
| 4,520,926 A | * | 6/1985 | Nelson | 206/366 |
| 4,702,385 A | * | 10/1987 | Shillington et al. | 220/481 |
| 4,737,390 A | * | 4/1988 | Fricano et al. | 428/34.2 |
| 4,746,008 A | * | 5/1988 | Heverly et al. | 206/1.5 |
| 4,828,107 A | | 5/1989 | Spencer | |
| 4,917,243 A | * | 4/1990 | Abrams et al. | 206/365 |
| 5,076,429 A | | 12/1991 | Patrick et al. | |
| 5,097,950 A | | 3/1992 | Weiss et al. | |
| 5,127,522 A | | 7/1992 | Ranford | |
| 5,145,063 A | * | 9/1992 | Lee | 206/364 |
| 5,323,902 A | * | 6/1994 | Palmer et al. | 206/366 |
| 5,411,193 A | * | 5/1995 | Culp | 224/669 |
| 5,603,404 A | | 2/1997 | Nazare et al. | |
| 5,673,790 A | * | 10/1997 | Schramm | 206/366 |
| 5,687,839 A | * | 11/1997 | Gnau et al. | 206/204 |
| 5,791,471 A | | 8/1998 | Radmand | |
| 6,010,444 A | * | 1/2000 | Honeycutt et al. | 588/255 |
| 6,250,465 B1 | | 6/2001 | Daniels et al. | |
| 6,279,743 B1 | * | 8/2001 | Ballard et al. | 206/364 |

(Continued)

FOREIGN PATENT DOCUMENTS

EP    569233 A1 * 11/1993

(Continued)

*Primary Examiner*—J. Gregory Pickett
(74) *Attorney, Agent, or Firm*—Greenlee Winner and Sullivan PC

(57) ABSTRACT

A disposal device used for the disposal of hazardous contaminated sharps, such as hypodermic needles, generated from treating patients. The disposal device is compact enough to fit in medical kits and hospital trays and is able to be used at the patient's bedside, thus eliminating the need to recap or transport contaminated sharps to non-bedside sharp disposal devices. The shape of the device provides enough stability to prevent the device from tipping over if bumped.

16 Claims, 12 Drawing Sheets

U.S. PATENT DOCUMENTS

| | | | |
|---|---|---|---|
| 2002/0134701 A1* | 9/2002 | Olsthoorn | 206/503 |
| 2004/0173488 A1* | 9/2004 | Griffin et al. | 206/363 |

FOREIGN PATENT DOCUMENTS

| | | | |
|---|---|---|---|
| GB | 2139965 A | * | 11/1984 |
| WO | WO 95/25331 A1 | | 9/1995 |
| WO | WO 03/096921 A2 | | 11/2003 |

* cited by examiner

BEDSIDE DISPOSAL OF CONTAMINATED SHARPS

CROSS-REFERENCE TO RELATED APPLICATIONS

This application claims benefit of U.S. Provisional Patent Application No. 60/523,251, filed Nov. 18, 2003.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable.

BACKGROUND OF THE INVENTION

Since HIV became an epidemiological concern in the early 1980's, the need to safely dispose sharp medical instruments while preventing injuries and the transmission of blood borne viral disease (Hepatitis B, C and HIV) to health care workers has become a serious health issue. In order to limit the number of injuries to health care workers, the Center for Disease Control recommends that disposable syringes with needles, scalpel blades, and other sharp items capable of causing injury should be placed intact into puncture resistant containers located as close as is practical to the area in which they were used. In current practice it is not practical to have disposal containers for contaminated sharps in every room where patients are treated or when patients are treated outside of a hospital, such as by a paramedic. Consequently, many injuries occur while a health care worker is trying to cap or transport sharp instruments from the patient's bedside to a disposal device, which is often located across the room or in another room.

A wide variety of containers for the disposal of sharp instruments are known in the art (WO 95/25,331 A1; WO 03/096,921 A2; U.S. Pat. Nos. 4,828,107; 5,076,429; 5,097,950; 5,145,063; 5,603,404; 5,791,471; and 6,250,465). Presently known containers are typically too large to be used at a patient's bedside or are designed to be mounted on a solid surface such as a wall. These containers are also typically designed to be used in a vertical orientation, i.e. they are tall relative to their length and width, so that a hypodermic needle, or other sharp instrument, inserted in the top of the container falls to the bottom due to gravity. Such containers are easily tipped over, which additionally makes them unsuitable for bedside disposal of sharp instruments.

What is needed is an easy-to-use, compact and portable disposal device for contaminated sharps that can be used by health care workers where patients are treated. It is believed that using a portable disposal device will prevent recapping and transport injuries since disposal will take place at the bedside or wherever the sharp instrument is used.

BRIEF SUMMARY OF THE INVENTION

The present invention is a device for the disposal of contaminated sharps. The device is compact and stable enough to fit on a tray and is suitable for bedside use. Furthermore, the device is compact enough for portable use, such as by paramedics or as part of a kit. The device is practical, disposable, has enough volume to hold contaminated sharps generated from treating a patient, and conforms to OSHA guidelines, which require that contaminated sharps be placed as soon as possible after use in containers that are puncture resistant, labeled or color coded, and leak proof on the sides and bottom of the container.

As used herein, the term "puncture resistant" means the device resists, inhibits, or prevents being torn, punctured, cut, or ripped. Examples of puncture resistant materials known in the art used for containers of contaminated sharps include, but are not limited to, hard plastic, metal, and cardboard. The device of the present invention also meets or exceeds the following criteria:

1) Functionality—the device has an appropriate size and shape for bedside use, is durable, easy to close, and resistant to chemical degradation;

2) Accessibility—the device provides easy access to the disposal opening, and is simple to use;

3) Visibility—workers are able to easily see and identify the device, any warning labels, such as biohazard labels, on the device, and the degree to which the device is full;

4) Accommodation—the device is conveniently stored and requires little or no assembly for use.

"Contaminated sharps" are any object or instrument contaminated with blood or other potentially infectious material that is capable of inflicting a puncture wound or penetrating the skin. Examples include but are not limited to needles, scalpels, capillary tubes, broken glass, dental wires, syringes (with or without the attached needle), pasteur pipettes, scalpel blades, razor blades, blood vials, test tubes, needles with attached tubing, and culture dishes.

The disposal device of the present invention comprises a compact container having a hollow elongated body with an open mouth at one end of the longitudinal axis. In the present context, the side of the container having the open mouth is the "front end" and the side opposite to the open mouth is the "back end". The front end of the container body is triangular in shape, while the back end of the body is in the shape of a rectangle, a triangle or a trapezoid. The bottom surface of the container body is the surface along the longitudinal axis that shares an edge with one side of the triangle at the front end and the long side of the trapezoid (or rectangle or triangle) at the back end.

The length from the front end to the back end is significantly greater than the height of the container (as measured from top to bottom at the front end), and the width of the container at the base is approximately equal to or greater than the height of the container. By "significantly greater" it is meant the ratio of the length of the device compared to the height of the device is at least 2:1, or, more preferably, at least 3:1. By "compact" it is meant that the device is small enough to easily fit on a hospital tray or in a kit and allow room for other instruments and items. In one embodiment of the invention, the container has a length ranging from about four to about ten inches, a width of about two to about four inches, and a height of about one to about three inches. In one embodiment, the container is approximately seven inches long from the front end to the back end, approximately three inches wide at the base and approximately one and a half inches tall. In another embodiment, the container is about ten inches long from the front end to the back end, about four inches wide at the base, and about three inches tall.

Contaminated sharps are inserted into the container through the open mouth at the front end. In addition to improved stability, the device of the present invention has improved ergonomics over the prior art. When in use, the device is easily orientated so that the front end is accessible to the health care worker without impeding the worker's ability to safely insert the contaminated sharps into the opening.

The container body is molded or formed from a hard plastic, although any suitable puncture resistant material can be used. The container is also molded or formed from a material, such as hard plastic, resistant to leaks and chemical degradation. At least one section of the container is color coded or otherwise labeled as a biohazard container for contaminated sharps. The majority of the container body is optionally transparent to allow visualization of items within the container. The container body, or at least the bottom side of the body, has a non-slip surface. By non-slip surface it is meant that the surface has enough friction when placed on a table or a tray that the device does not easily slide across the table or tray. The non-slip surface includes, but is not limited to, a thin layer of rubber or a sticky resin sprayed onto the bottom of the container body.

The front end of the container body is triangular in shape. Having the container, or at least a portion of the container, be significantly wider at the base than the top of the container allows for greater stability and allows the device to remain upright even if bumped. In one embodiment of the present invention, the entire container is triangular in shape. In another embodiment, the front end is triangular while the back end is rectangular in shape. The container may also be tapered so that the front end is bigger than the back end.

Across the open mouth at the front end is a cover guard. The cover guard covers the open mouth of the container except for a hole through the center of the cover guard. A plurality of slots extending radially from the hole form flaps from the sections of the cover guard between the slots. The central hole and slots in the cover guard allow for easy and safe insertion of contaminated sharps, such as needles, into the container while ensuring contaminated sharps remain inside the container. The cover guard is made from flexible material so that objects larger than the hole can still be inserted into the container by pushing the flaps inward.

The cover guard is attached to the front end of the container so that it remains securely over the open mouth and cannot be easily removed. In an embodiment of the present invention, the cover guard is a separate piece from the container and is made from a different type of plastic than the body of the container. In this embodiment, the cover guard is made from a soft pliable plastic or rubber, whereas the body of the container is made from a hard plastic. The cover guard is sized to tightly fit over or within the front end of the container. In one embodiment of the present invention, at least one side of the cover guard is permanently attached, i.e., plastic welded, to the container body.

The slots are of varying length and thickness. The slots may be sized to accommodate a specific type of contaminated sharp, such as a suture needle. The hole may be circular or the slots may intersect at the hole to form an irregular shape or a star shape. The bottom of the hole in the cover guard is higher than the bottom inner surface of the container so that a contaminated sharp inserted through the hole will fall to the bottom inner surface and remain below the hole. This prevents sharps inserted into the container from falling back out through the hole in the cover guard.

Over the front end and cover guard is a device cap. The cap is made from a hard plastic or other puncture resistant material. The device cap may be made from the same material as the container body or from another suitable puncture resistant material. The cap is orientated in an open or closed position and can be attached to part of the container body. In the closed position, the cap securely fits over the front end and the cover guard and blocks the open mouth of the container. Once closed, additional force is required to re-open the cap, thereby insuring that the cap will not open during transport or disposal. In the open position, the cap does not block the cover guard and open mouth of the container.

In an embodiment of the present invention, one end of a flexible band of material is connected to the device cap, while the other end is connected to the outside surface of the container near the front end. In a further embodiment of the present invention, one side of the cap is hinged to the front end allowing the cap to close over the cover guard and open mouth.

In an embodiment of the present invention, the cap is adapted to tightly fit around the front end of the container while in a closed position. In another embodiment, the side of the device cap facing the container while in a closed position has a groove running around the perimeter of the cap. The groove has a shape and dimensions that correspond to the shape and dimensions of a rim formed by the outer surface of the front end. When the device cap is in a closed position, the rim of the front end of the container fits into the groove of the device cap. In the closed position, the cap fits over the front end and guard cover and the rim snaps into the groove, thereby securing the device cap to the front end of the container body.

In another embodiment of the present invention, at least one locking prong, having a lipped end, extends from the front end of the container body. The device cap has at least one prong opening corresponding to the size and position of the locking prong. When the device cap is closed over the front end of the container, the locking prong fits through the prong opening and the lipped end of the prong contacts the surface surrounding the prong opening on the side of the device cap that faces away from the container. The contact between the lipped end and the surface surrounding the prong opening prevents the device cap from being re-opened unless significant additional force is used.

The device can be used to immediately collect contaminated sharps after a patient is treated. Once the contaminated sharps have been inserted into the container, the cap is closed over the front end, and the device can be transported and placed in a larger secondary disposal container.

The device can be manufactured to be sterile, such as through radiation sterilization, and suitable for use where sterilization is a concern. The device can be wrapped and packaged for individual use, or the device can be packaged as part of a kit that includes sharp instruments. Such kits include but are not limited to a lumbar puncture kit, a central line kit, a paracentisis kit, a thoracentisis kit, a thoracotomy kit and a suture kit.

DETAILED DESCRIPTION OF THE INVENTION

The invention may be further understood by the following non-limiting examples.

All references cited herein are hereby incorporated by reference to the extent not inconsistent with the disclosure herewith.

Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Figure 1:
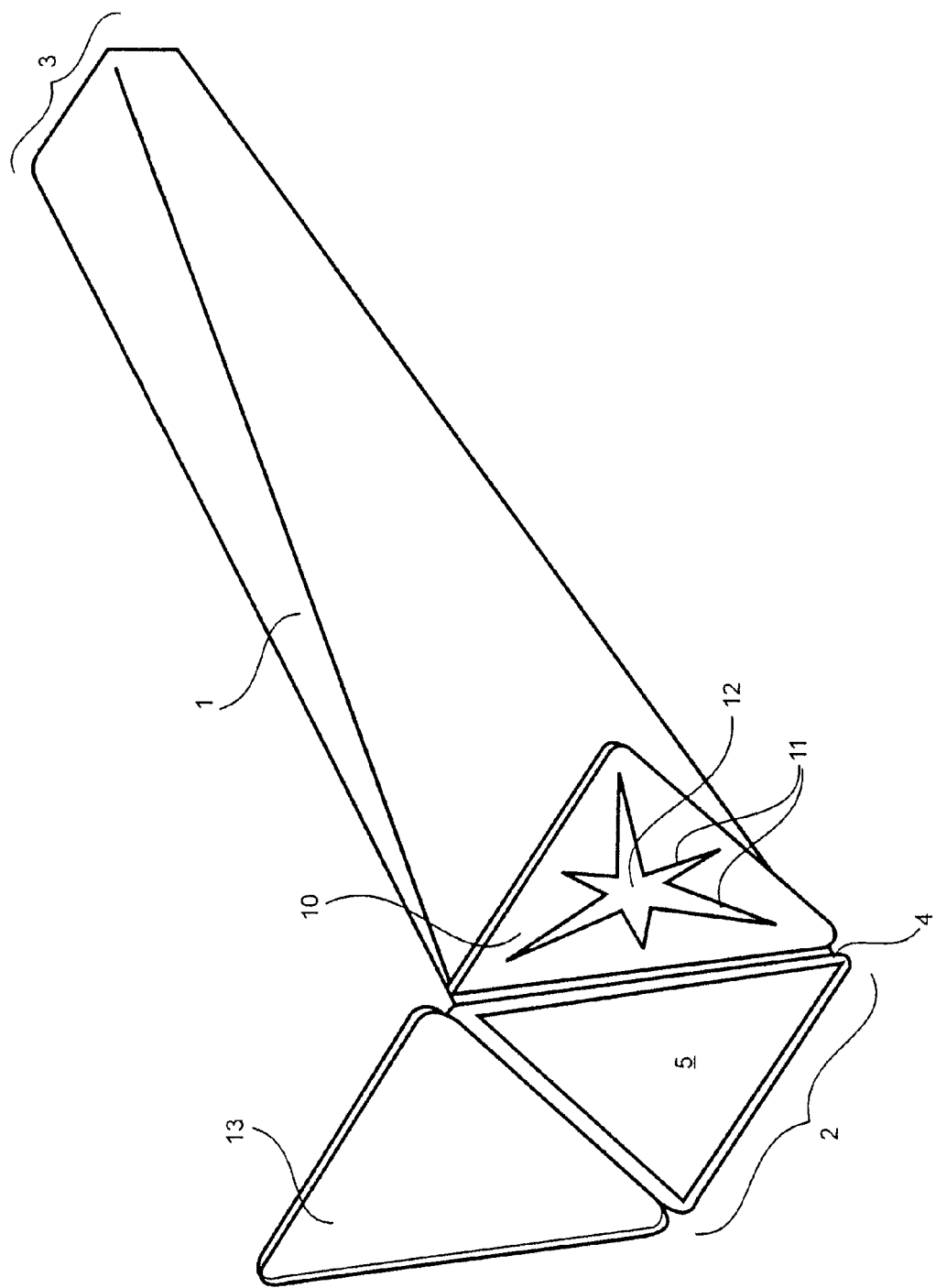
FIG. 1 shows a contaminated sharps disposal device of the present invention having a triangular front end and a rectangular back end, where one side of the device cap and the cover guard are attached to the front end of the container. Neither the device cap nor the cover guard is closed over the open mouth of the container.
Figure 2:
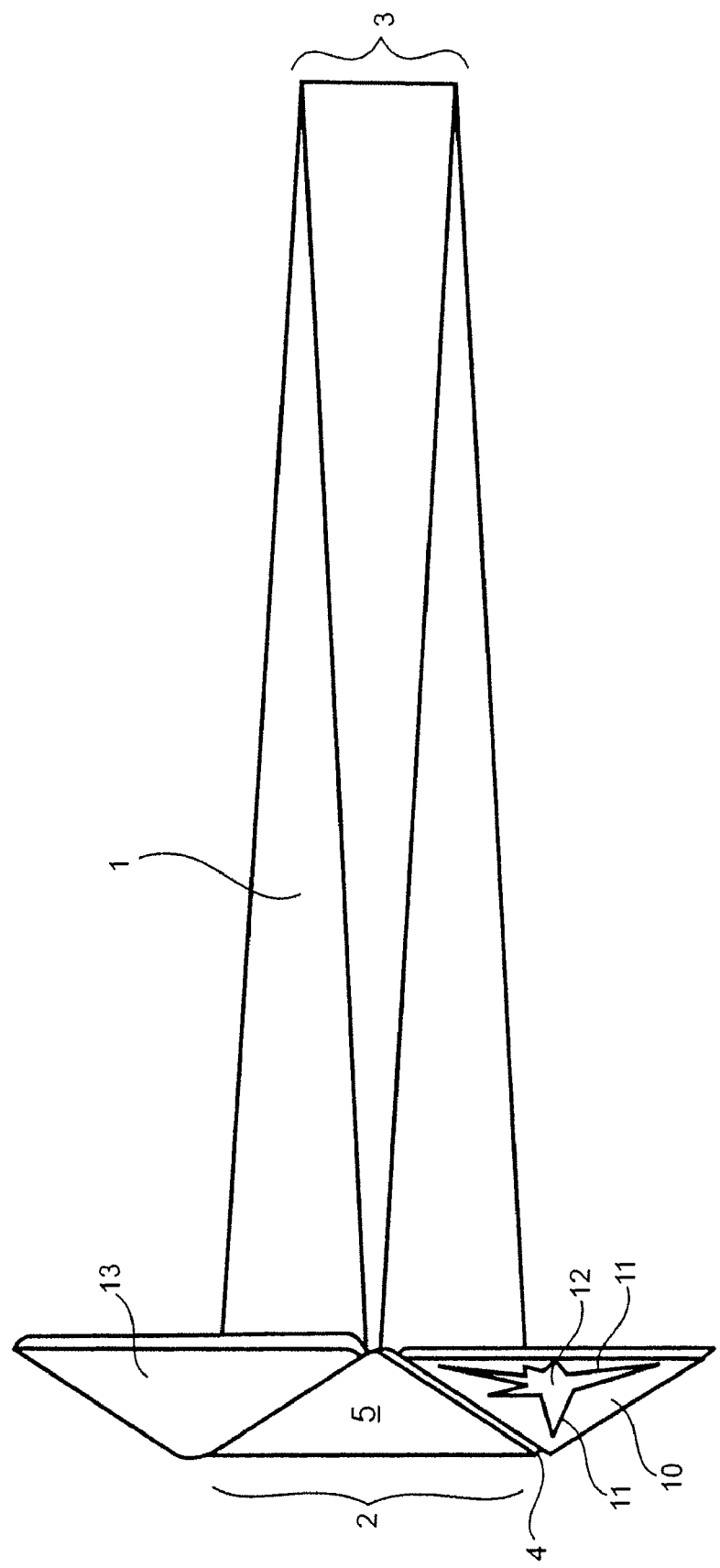
FIG. 2 shows a top view of the disposal device of FIG. 1.

FIGS. 1 and 2 show an embodiment of a contaminated sharps disposal device of the present invention. The device comprises a container body 1 having a front end 2 and a back end 3. In this embodiment, the front end 2 is triangular in shape and the back end 3 is rectangular. The device includes an open mouth 5 at the front end 2 of container body 1. The edge of the container body 1 around the open mouth 5 is raised forming a rim 4. Cover guard 10 can be attached to container body 1 to allow cover guard 10 to open and close over open mouth 5. Through cover guard 10 is hole 12 and a plurality of slots 11. Device cap 13 is also attached to container body 1 to allow device cap 13 to open and close over cover guard 10 and open mouth 5. In FIGS. 1 and 2, cover guard 10 and device cap 13 are not closed over open mouth 5.

Figure 3:
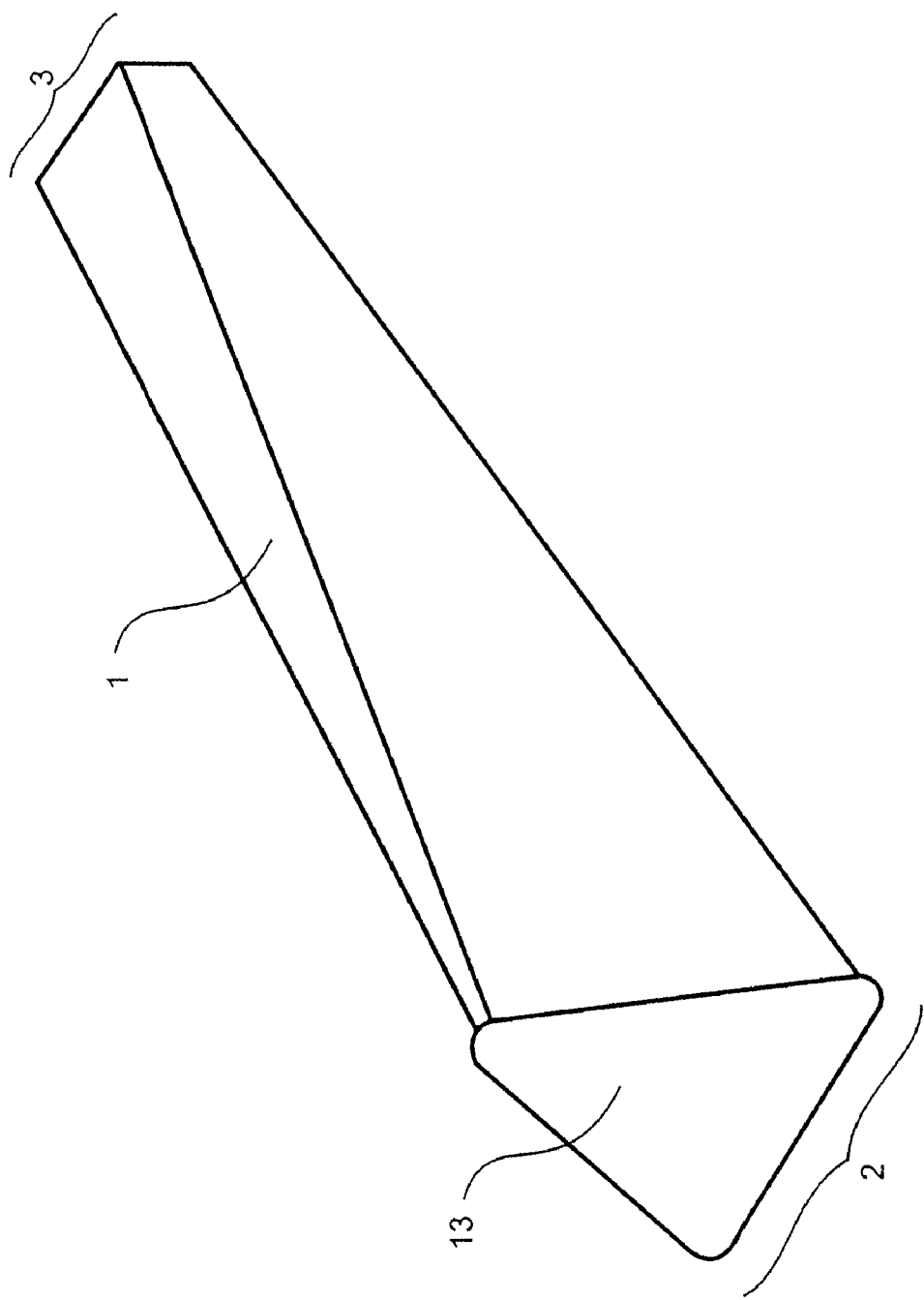
FIG. 3 shows the disposal device of FIG. 1 where the device cap and the cover guard are closed over the open mouth of the container.
Figure 4:
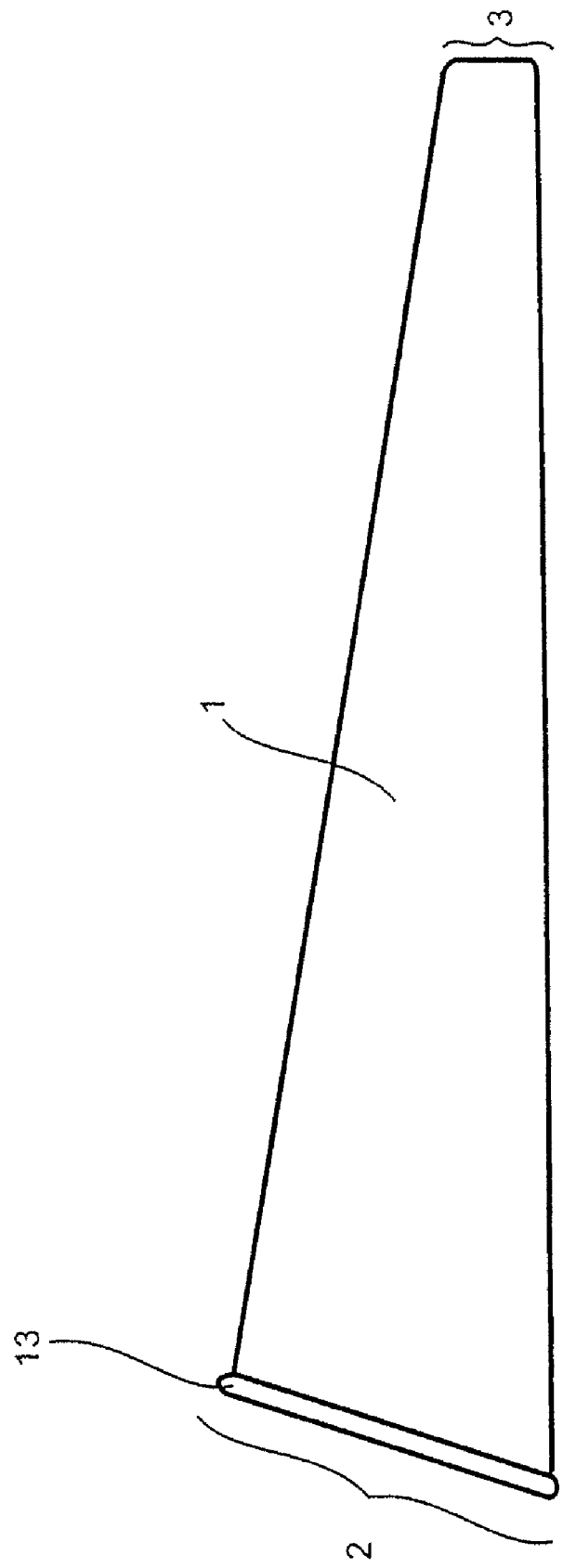
FIG. 4 shows a side view of the disposal device of FIG. 3.

FIGS. 3 and 4 show the disposal device of FIGS. 1 and 2 where the cover guard 10 (not shown) and device cap 13 are closed over open mouth 5.

Figure 5:
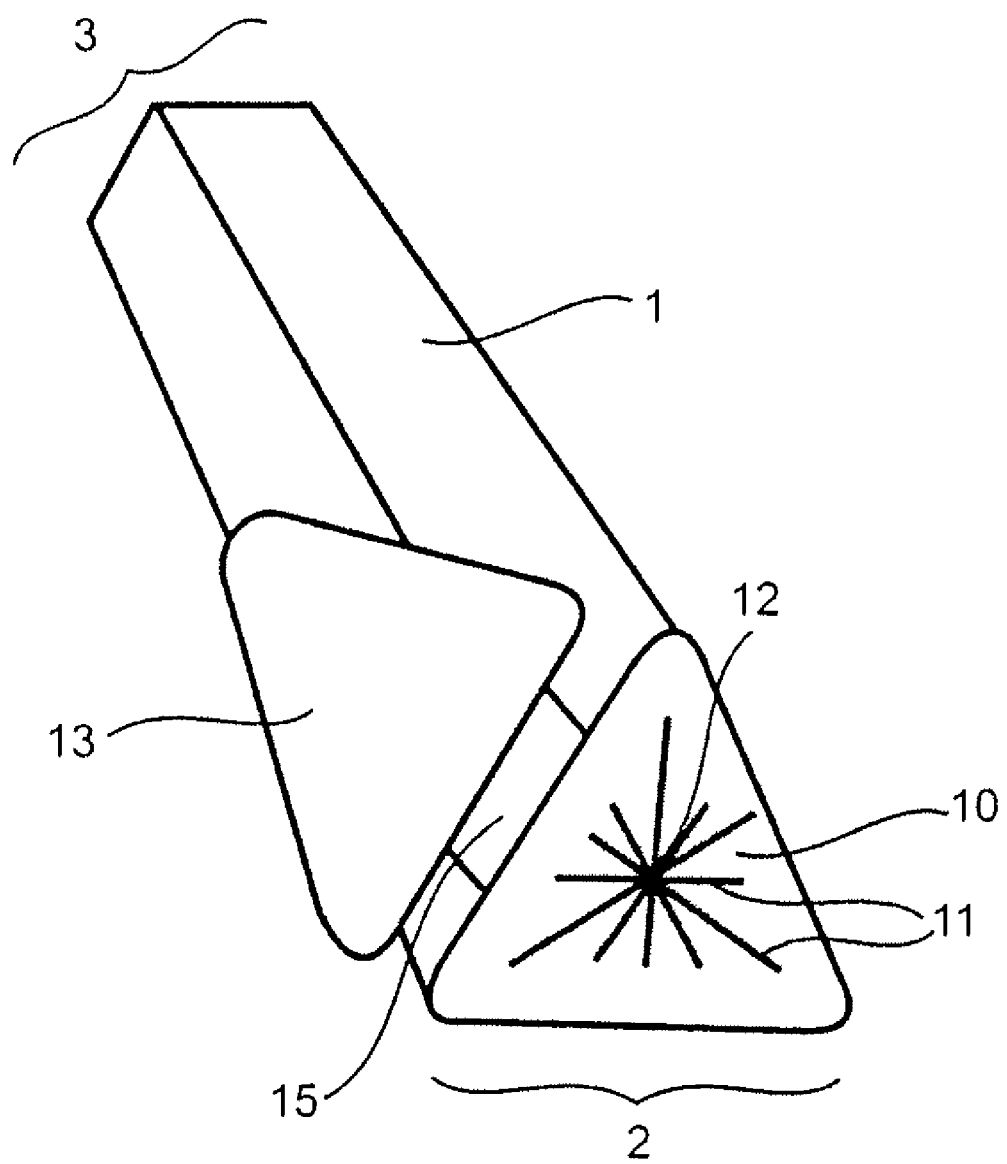
FIG. 5 shows a front view of a contaminated sharps disposal device of the present invention where the cover guard covers the open mouth of the container while the device cap is open.
Figure 6:
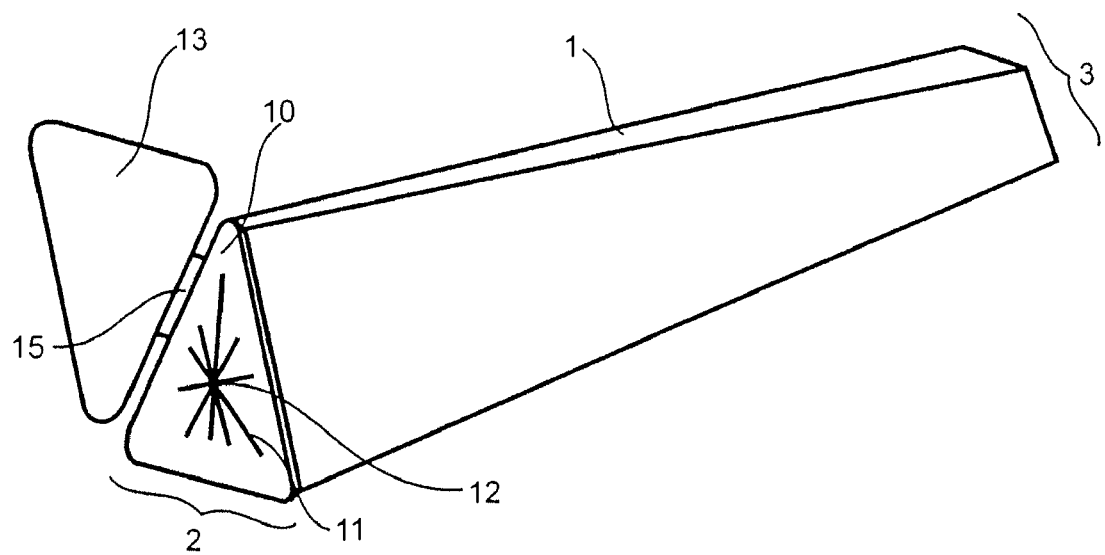
FIG. 6 shows a side view of the disposal device of FIG. 5.

FIGS. 5-6 show another embodiment of a contaminated sharps disposal device of the present invention. In this embodiment, the cover guard 10 is closed over the open mouth 5 (not shown) while the device cap 13 remains open. Device cap 13 is attached to container body 1 by a flexible band 15. Hole 12 in cover guard 10 is circular and slots 11 are thinner than the slots 11 illustrated in FIGS. 1-2.

Figure 7:
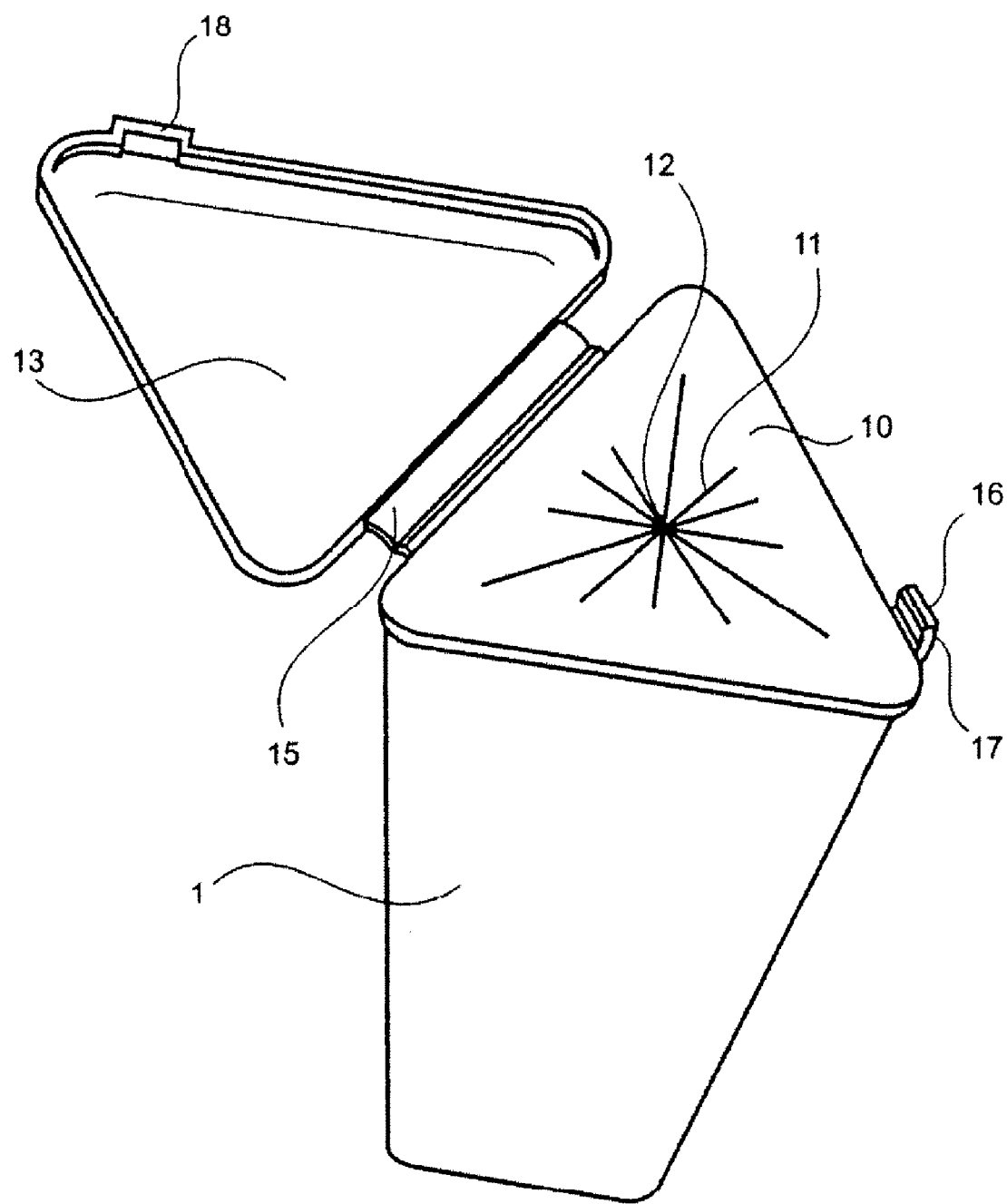
FIG. 7 and FIG. 8 show a contaminated sharps disposal device of the present invention having a locking prong on the front end of the container and a corresponding prong opening on the device cap.
Figure 8:
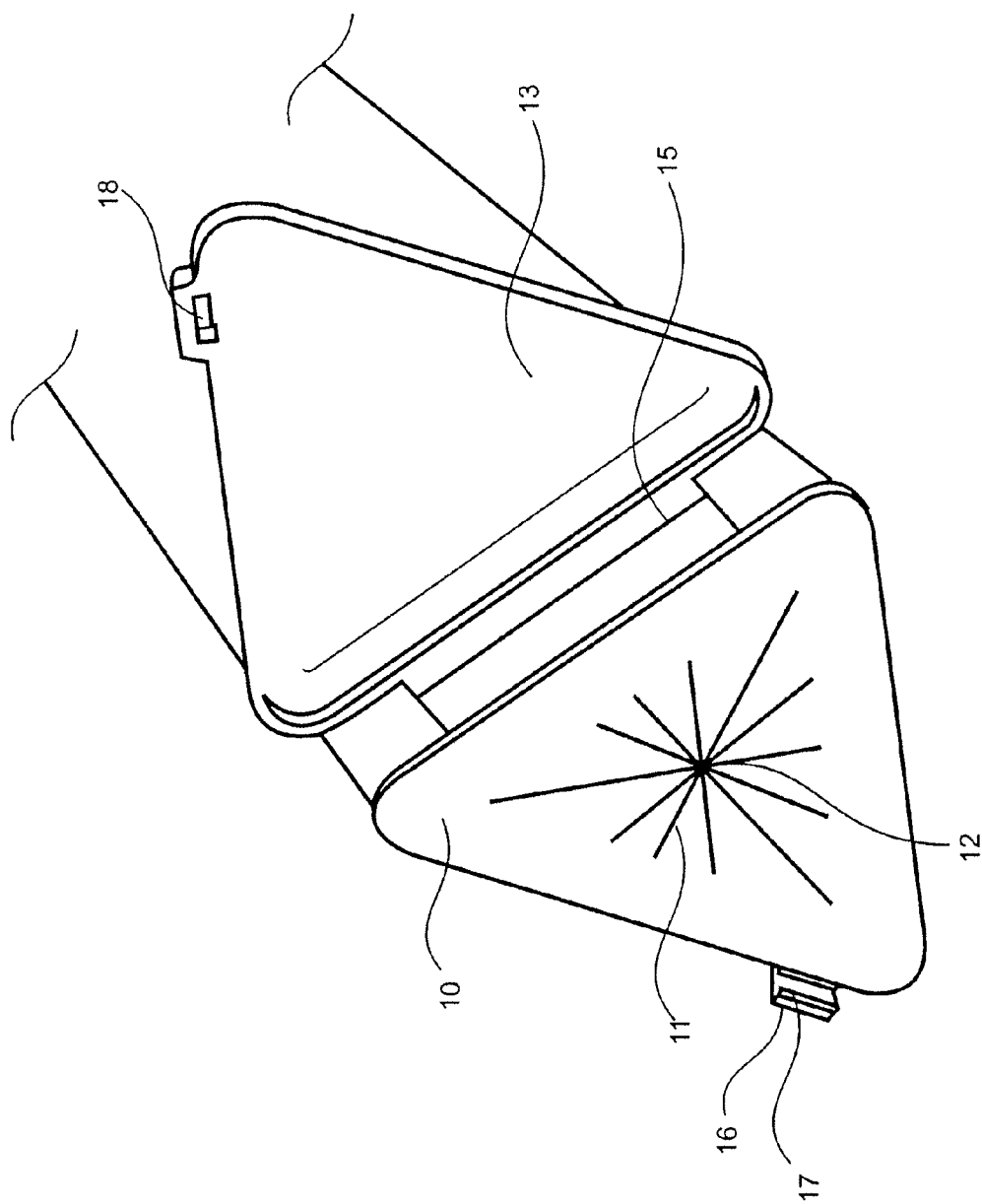
Figure 9:
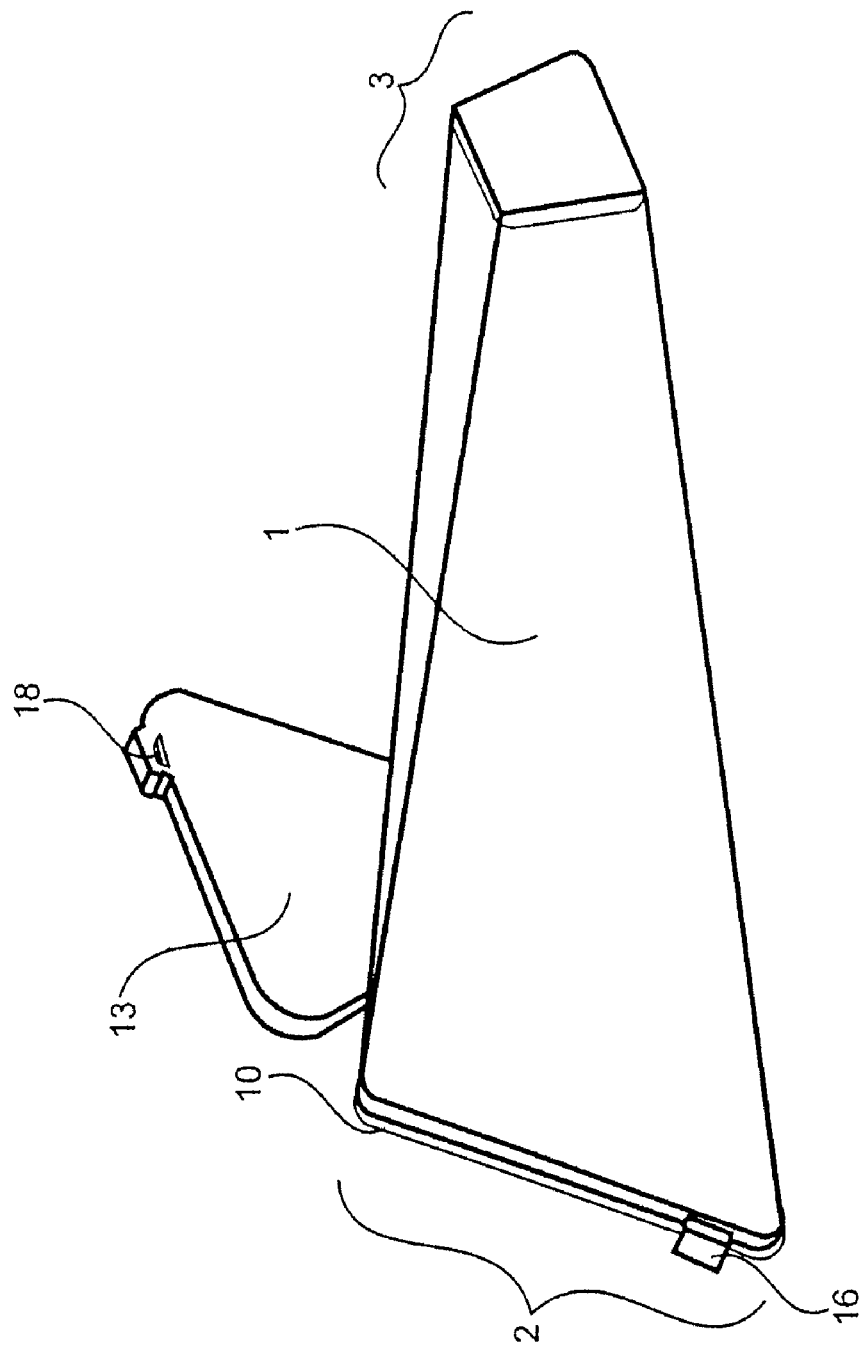
FIG. 9 shows a rear-side view of the device of FIGS. 7 and 8.
Figure 10:
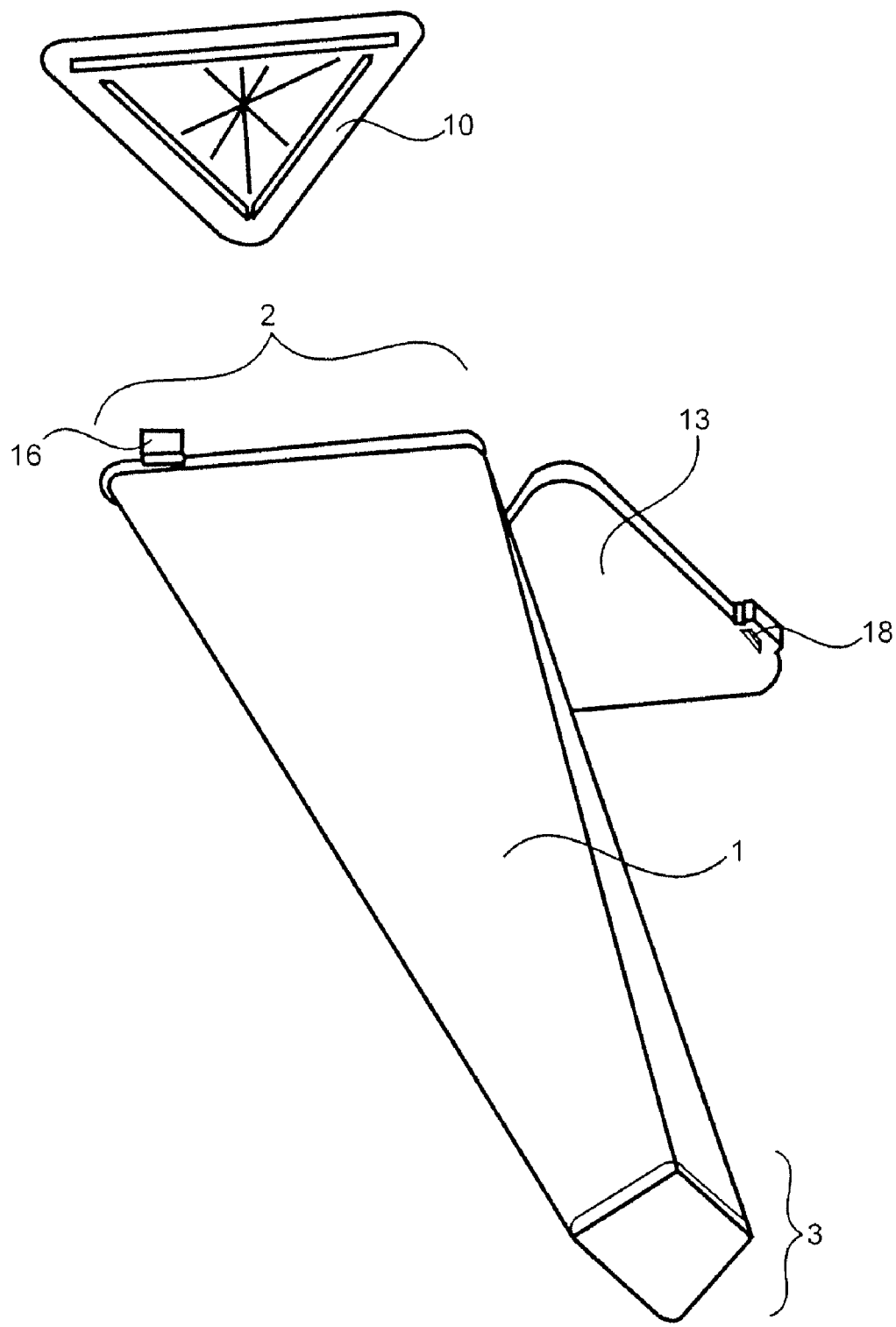
FIG. 10 shows the device of FIGS. 7 and 8 with the cover guard detached from the front end of the container.
Figure 11:
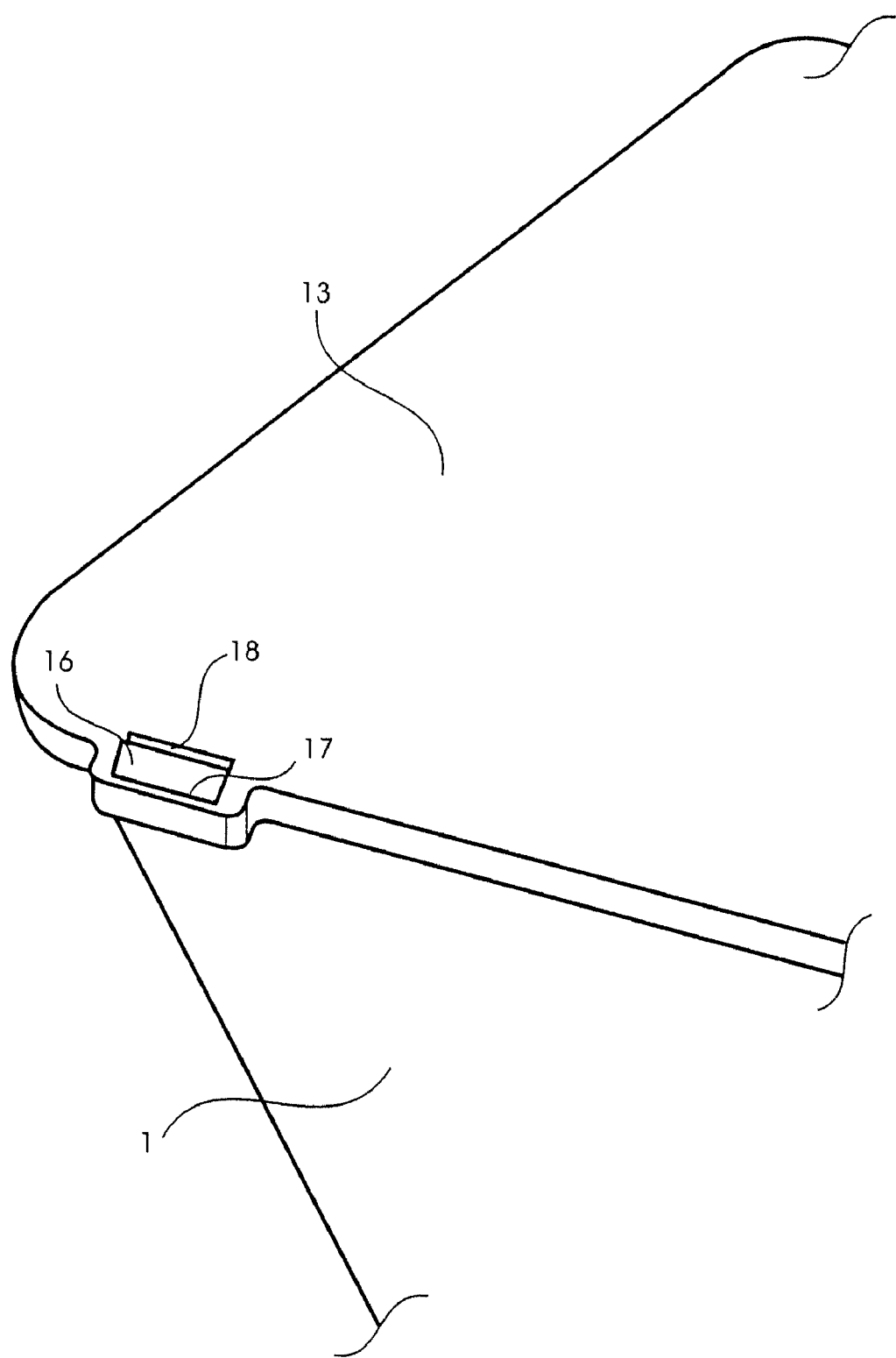
FIG. 11 shows the front end of the device of FIGS. 7 and 8 with the device cap closed and the lipped end of the locking prong protruding from the prong opening.

FIGS. 7-11 show one embodiment of the present invention comprising a device cap 13 having a prong opening 18 and the front end 2 of the container body 1 having a locking prong 16. The tip of locking prong 16 forms a lipped end 17. FIGS. 7-9 illustrate this embodiment where device cap 13 remains open. FIG. 10 shows the device with the device cap 13 open and the cover guard 10 detached from the container body 1. FIG. 11 illustrates the device having the device cap 13 closed over the cover guard (not shown). In FIG. 11, the lipped end 17 of prong 16 protrudes through prong opening 18. Contact between the lipped end 17 and the surface of device cap 13 (on the side of device cap 13 that faces away from the container body) surrounding the prong opening 18 prevents the device cap from being re-opened.

Figure 12A:
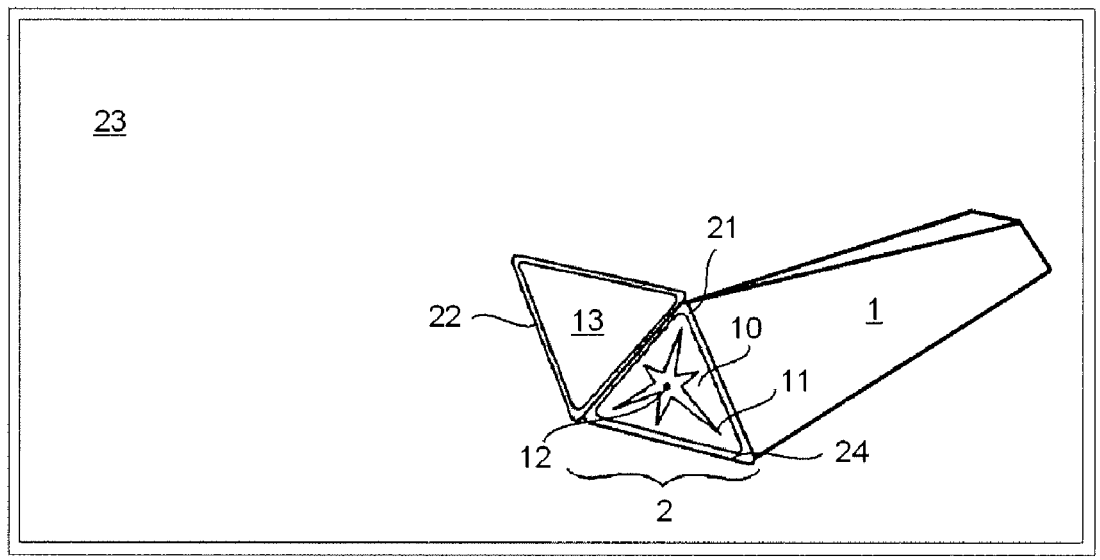
FIG. 12A shows a device of the present invention and FIG. 12B shows examples of contaminated sharps that may be disposed in the device.
Figure 12B:
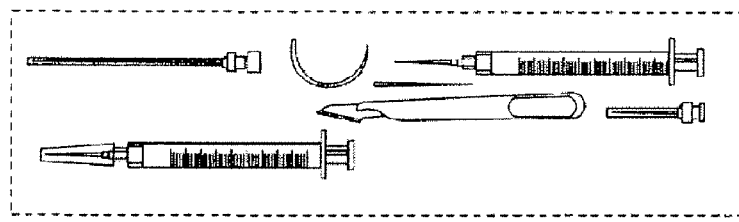

A device of the present invention is illustrated in FIGS. 12A having a length of about seven inches from the front end 2 to the back end 3, a width of about three inches at the base, and a height of about an inch and a half. This size is compact enough for use as part of a portable medical kit 23 or to fit on a hospital tray located bedside to a patient being treated. Meanwhile, the device is large enough to hold a variety of contaminated sharps, illustrated in FIG. 12B, generated from treating the patient. The device in this embodiment contains cover rim 21 on the front end 2. The cover rim 21 corresponds to a groove 22 around the device cap 13, so that when device cap 13 is closed over cover guard 10, cover rim 21 fits inside groove 22.

While the invention has been described with certain preferred embodiments, it is understood that the preceding description is not intended to limit the scope of the invention. It will be appreciated by one skilled in the art that various equivalents and modifications can be made to the invention shown in the specific embodiments without departing from the spirit and scope of the invention.

We claim:

1. A contaminated sharps disposal device comprising:
a compact hollow container made from puncture resistant material having a base, an open front end and a closed back end, wherein the length from the front end to the back end is significantly greater than the height of the container, and the width of the container at the base is approximately equal to or greater than the height of the container, wherein the front end of said device is triangular in shape and the container is tapered so that the back end is smaller than the front end, and the back end of said container is in the shape of a rectangle or trapezoid;
a cover guard attached over said open front end having a hole through its center and a plurality of slots radially extending from said hole; and
a device cap adapted to securely close over said cover guard and said open front end.

2. The device of claim 1 further comprising one or more contaminated sharps disposed within said container.

3. The device of claim 1 wherein said cover guard is sized to tightly fit over or within the open front end of said container.

4. The device of claim 1 wherein at least one edge of said cover guard is permanently attached to the front end of said container.

5. The device of claim 3 wherein said cover guard is plastic welded to the front end of said container.

6. The device of claim 1 wherein said cover guard is made from pliable soft plastic.

7. The device of claim 1 wherein said container is made from rigid hard plastic.

8. The device of claim 1 wherein one end of a flexible band of material is connected to said device cap while the other end is connected to the outside surface of said container.

9. The device of claim 1 wherein said device cap is hinged to the front end of said container.

10. The device of claim 1 further comprising a rim on said container around the open front end and a corresponding groove on the side of said device cap that faces the cover guard when in a closed position, wherein said groove matches the size and shape of said rim.

11. The device of claim 1 further comprising a locking prong extending from the front end of the container body, and a corresponding prong opening on said device cap, wherein said locking prong has a lipped end.

12. The device of claim 1 wherein the length from the front end to the back end is about seven inches or less, the width of the container is about three inches at the base or less, and the height of the container is about an inch and a half.

13. A medical kit used in treating a patient comprising the disposal device of claim 1.

14. The kit of claim 13 further comprising sharp objects used in treating a patient.

15. The kit of claim 14 wherein said kit is a lumbar puncture kit, a central line kit, a paracentisis kit, a thoracentisis kit, a thoracotomy kit or a suture kit.

16. A method of disposing contaminated sharps comprising the steps:
   (a) placing an empty compact contaminated sharps disposal device next to a patient, wherein said device comprises:
      (i) a compact hollow container made from puncture resistant material having a base, an open front end and a closed back end, wherein the length from the front end to the back end is significantly greater than the height of the container and the width of the container at the base is equal to or greater than the height of the container, wherein the front end of said device is triangular in shape and the container is tapered so that the back end is smaller than the front end, and the back end of said container is in the shape of a rectangle or trapezoid;
      (ii) a cover guard attached over said open front end having a hole through its center and a plurality of slots radially extending from said hole; and
      (iii) a device cap adapted to securely close over said cover guard and said open front end;
   (b) treating said patient in way that generates contaminated sharps;
   (c) placing said contaminated sharps into said disposal device;
   (d) closing a device cap over said disposal device; and
   (e) transporting said disposal device to a secondary disposal device.

* * * * *